United States Patent [19]

Sperinde et al.

[11] Patent Number: 4,523,279
[45] Date of Patent: * Jun. 11, 1985

[54] APPARATUS FOR DETERMINING OXYGEN SATURATION LEVELS IN BLOOD

[75] Inventors: Johnie M. Sperinde, San Jose; Stanley D. Goldring, Cupertino; Dean T. Miller, Portola Valley, all of Calif.

[73] Assignee: Oximetrix, Inc., Mountain View, Calif.

[*] Notice: The portion of the term of this patent subsequent to Jun. 5, 2001 has been disclaimed.

[21] Appl. No.: 616,817

[22] Filed: Jun. 4, 1984

Related U.S. Application Data

[63] Continuation of Ser. No. 210,032, Nov. 24, 1980, Pat. No. 4,453,218.

[51] Int. Cl.³ .............................................. A61B 5/04
[52] U.S. Cl. .................................... 364/416; 128/696; 356/41
[58] Field of Search ................. 364/416, 417; 356/41; 128/634, 696; 328/149, 167; 455/224

[56] References Cited

U.S. PATENT DOCUMENTS

| | | | |
|---|---|---|---|
| 3,848,586 | 11/1974 | Suzuki et al. | 364/417 X |
| 4,109,643 | 8/1978 | Bond et al. | 356/41 X |
| 4,114,604 | 9/1978 | Shaw et al. | 356/41 X |
| 4,151,471 | 4/1979 | Packard et al. | 455/224 |
| 4,167,331 | 9/1979 | Nielsen | 356/41 X |
| 4,266,554 | 5/1981 | Hamaguri | 364/416 X |

*Primary Examiner*—Edward J. Wise
*Attorney, Agent, or Firm*—Robert S. Kelly

[57] ABSTRACT

A signal filter method and apparatus for removing portions of a signal indicative of erroneous data, an exemplary apparatus including means for receiving the signal, means for adjusting a threshold by increasing the threshold a first predetermined amount when the signal is in a predetermined relationship with the threshold and for decreasing the threshold a second predetermined amount when the signal is in a second predetermined relationship with the threshold, and means for comparing the signal with the adjusted threshold and for transmitting the signal if the signal bears a first predetermined relationship to the threshold. Disclosed herein are digital and analog implementations of the signal filter method and apparatus, particularly suited for use with catheter-type oximeter apparatus.

8 Claims, 5 Drawing Figures

FIG_2

APPARATUS FOR DETERMINING OXYGEN SATURATION LEVELS IN BLOOD

This is a continuation of application Ser. No. 210,032, filed Nov. 24, 1980 now U.S. 4,453,218.

BACKGROUND

The present invention relates generally to apparatus for determining oxygen saturation levels in blood, or oximeters, and more particularly to apparatus suitable for use with in vivo catheter-type oximeters which determines the oxygen saturation level by utilizing reflected electromagnetic radiation at a plurality of different wavelengths.

Various catheter-type oximeter apparatus are known for determining blood oxygen saturation. One such apparatus is disclosed in U.S. Pat. No. 4,144,604 to Shaw, et al., the disclosure of which is incorporated herein by reference. Typically with such apparatus, a catheter is introduced into a blood vessel and the blood within the vessel flows about the catheter tip. The catheter includes a first fiberoptic guide which conducts radiation from the oximeter apparatus to an aperture at the catheter tip. The blood flowing about the catheter tip scatters a portion of the incident radiation thereon back to a second aperture at the catheter tip where a second fiberoptic guide transmits this back-scattered radiation to the oximeter apparatus. The back-scattered radiation is then analyzed by the oximeter apparatus to provide a measurement of oxygen saturation.

As the blood under test flows about the catheter tip, the amount of radiation returning therefrom exhibits pulsatile fluctuations synchronized with the heartbeat. It is believed that these fluctuations result from the catheter tip impacting or very closely approaching the vessel wall. Since the vessel wall exhibits reflective characteristics not necessarily related to blood oxygen saturation, these substantial fluctuation resulting in greatest part from the reflectance of the vessel wall can introduce inaccuracies into the measurement of blood oxygen.

Various techniques have been utilized in oximeters in the past which have resulted in reducing the effects of or eliminating these substantial fluctuations. In one system, the time constant or span of the oxygen saturation measurement is relatively long thereby reducing the influence that the substantial radiation fluctuations may have on the oxygen saturation calculation. However, this technique does not remove from the oxygen saturation measurement process the erroneous data represented by the substantial radiation fluctuations. Thus, the oxygen saturation calculation is based at least in part upon erroneous data, thereby adversely affecting the accuracy of the oxygen saturation measurement.

In another oximeter apparatus, the catheter tip is enclosed within a cage-type structure in an attempt to prevent the oximeter tip from impacting the vessel wall. While the cage structure may effectively separate the catheter tip from the vessel wall, the structure also greatly increases the tendency for deposits to form on the catheter tip, an undesirable result.

SUMMARY OF THE INVENTION

With the apparatus of the present invention an oximeter is provided which first detects the substantial fluctuations which occur when the catheter tip is receiving reflected radiation from other than blood and then prevents the data received during the interval of each fluctuation from being processed with the circuitry which determines the continuous oxygen saturation level of the blood.

Thus, the apparatus includes a means for generating radiation at a plurality of different wavelengths and a catheter which is adapted to be used in vivo in a patient's bloodstream and includes a fiberoptic guide or the like for transmitting the radiation to the distal catheter tip and another fiberoptic guide or the like for receiving the reflected radiation at the catheter tip and directing it back to a detector which generates a plurality of data signals corresponding to the intensities of the radiation received at each of the different wavelengths. These signals are monitored to detect those short time intervals when the signals substantially increase in value, and those signals thus detected during the short time intervals are eliminated from the signal processing circuitry which operates with the data signals to provide a continuous blood oxygen saturation measurement.

DESCRIPTION

Figure 1:
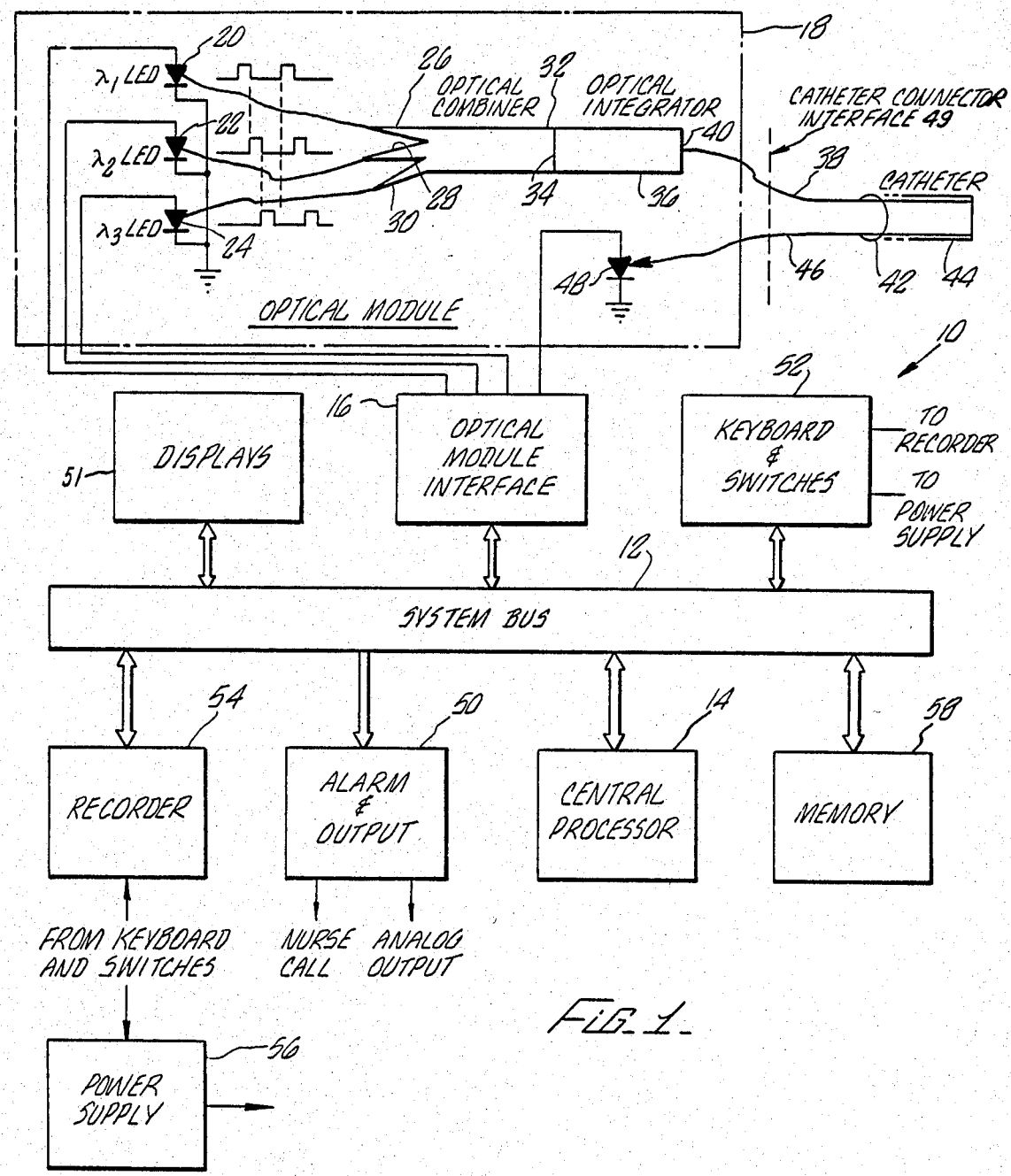
FIG. 1 is a block diagram of an oxygen saturation measurement apparatus of the present invention.

With reference now to FIG. 1, the oxygen saturation measuring apparatus 10 of the present invention, sometimes herein referred to as an oximeter or oximeter apparatus, is preferably a microprocessor bus-oriented system, a configuration which is well known to those skilled in the art. More particularly, the apparatus 10 includes a system bus 12 comprising a plurality of conductors for transmitting address, data, program and control information to various portions of the apparatus 10. The apparatus 10 is controlled by a central processor 14, which is connected to and substantially controls the system bus 12. In an exemplary embodiment, the central processor 14 is a type 6800 manufactured by Motorola Semiconductor Products, Inc.

The system bus 12 communicates with an optical module interface 16 which in turn is connected to an optical module 18. The interface 16 drives a plurality of light-emitting diodes (LEDs) 20, 22, and 24, which emit radiation at preselected wavelengths $\lambda_1$, $\lambda_2$ and $\lambda_3$ respectively. This radiation is collected by fiberoptic guides 26, 28, and 30, which conduct the radiation emitted by the diodes 20-24 to an optical combiner 32. The optical combiner 32 in turn transmits radiation through an end cross-section 34 to an optical integrator 36. A transmitting fiberoptic guide 38 is coupled to the exit aperture 40 of the optical integrator 36 and the fiberoptic guide 38 consequently transmits radiation through a catheter 42 to an aperture within a distal tip 44 of the catheter 42. The catheter tip 44 is disposed within a blood vessel and the blood under test flows through the vessel and about the tip 44.

The radiation emitted from the fiberoptic guide 38 is back-scattered by the blood under test and is reflected by the vessel walls. This back-scattered and reflected radiation is then received through a second aperture within the catheter tip 44 by a second fiberoptic guide 46. The fiberoptic guide 46 transmits this radiation to a detector 48 which provides a signal proportional thereto to the optical module interface 16.

With continued reference to FIG. 1, the apparatus 10 further includes various displays 48 responsive to the system bus 12. Furthermore, the system bus 12 is connected to an alarm and output circuit 50 which may provide an audio alert tone for the operator of the apparatus 10, nurse call signals and a suitable auxiliary analog output for driving ancillary equipment. A keyboard and control switches 52 is connected to the system bus 12 and also is directly connected to a recorder 54 and to a power supply 56. The recorder 54 is also responsive to the system bus 12 to produce a permanent strip chart record of the blood oxygen saturation as measured by the apparatus 10. The power supply 56 provides power throughout the apparatus 10.

The central processor 14, through the system bus 12, communicates with a memory 58 which may include program instructions for the central processor 14 in read-only memory (ROM) and which may further include temporary or scratch-pad random-access memory (RAM) for use by the central processor 14 during the operation of the apparatus 10.

In operation, the apparatus 10 is controlled by the keyboard and switches 52 to energize the power supply 56. The optical module interface 16 sequentially energizes the diodes 20-24 to sequentially provide radiation at the three preselected wavelengths $\lambda_1$, $\lambda_2$ and $\lambda_3$ via the catheter 42 to the catheter tip 44. Upon back scattering by the blood under test and tranmission via the catheter 42 to the detector 48, the optical module interface 16 coverts the analog signal from the detector 48 indicative of radiation intensity into a digital signal which in the embodiment of FIG. 1 may be 12 bits. This digital signal is then applied through the system bus 12 as controlled by the central processor 14 and is stored into the memory 58. The central processor 14 subsequently uses this data stored in the memory 58 to calculate the blood oxygen saturation. For example, the central processor 14 may implement equation 8 from the referenced Shaw, et al., patent, which is as follows:

$$OS = \frac{A_0 + A_1\left(\frac{I_1}{I_2}\right) + A_2\left(\frac{I_1}{I_2}\right)^2 + A_3\left(\frac{I_3}{I_2}\right)}{B_0 + B_1\left(\frac{I_1}{I_2}\right) + B_2\left(\frac{I_1}{I_2}\right)^2 + B_3\left(\frac{I_3}{I_2}\right)}$$

where $A_0$, $A_1$, $A_2$ and $A_3$ are weighting factors or coefficients, $B_0$, $B_1$, $B_2$ and $B_3$ are weighting factors or coefficients, and $I_1$, $I_2$, and $I_3$ are radiation intensities from the blood under test measured at wavelengths $\lambda_1$, $\lambda_2$ and $\lambda_3$, respectively, each normalized with respect to a reference light intensity measurement. Once the calculation is completed, the central processor 14 provides the resulting oxygen saturation (OS) value to the displays 48, and if enabled, to the recorder 54. If the central processor 14 detects that an alarm condition exists, the alarm and output circuit 50 generates an audio alarm tone or a nurse call signal.

It will be understood by those skilled in the art that the apparatus of FIG. 1 is generally a digital implementation of the catheter oximeter apparatus and method which is disclosed in the referenced Shaw, et al., patent. Such a microprocessor-based bus-oriented system will be readily apparent to one skilled in the art. Moreover, other than three radiation intensities may be used which can provide an oxygen saturation measurement through other suitable mathematical relationships.

Figure 2:
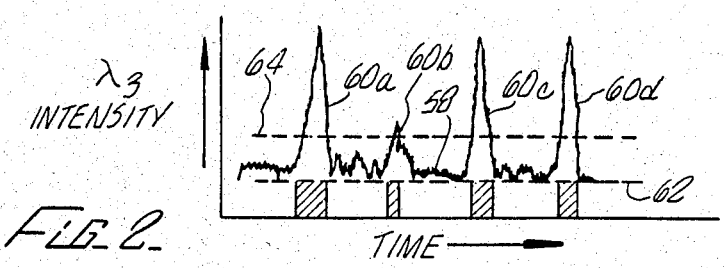
FIG. 2 is an exemplary wave form depicting intensity fluctuations in radiation returning from a catheter tip.

With reference now to FIG. 2, an intensity curve 58 of the back-scattered and reflected radiation from, for example, LED 24 operating at wavelengths $\lambda_3$, includes pulsatile fluctuations 60a-60d synchronized with the patient's heartbeat. Although the $\lambda_3$ intensity curve 58 is indicated by a continuous line, it is to be understood that the $\lambda_3$ intensity as detected by the detector 48 in the exemplary embodiment of FIG. 1 is a series of individual intensity measurements which, when plotted together, form the $\lambda_3$ intensity curve 58 of FIG. 2. The pulsatile fluctuations 60a-60d, if of sufficient magnitude, represent erroneous or unsuitable reflected radiation intensities which typically result from the catheter tip 44 impacting or very closely approaching the vessel walls as the catheter tip 44 is moved about within the vessel during a hearbeat. The $\lambda_3$ intensity shown in FIG. 2 is converted by the optical module interface 16 of FIG. 1 into a corresponding digital value which may then be utilized by the central processor 14 as is described below.

Figure 3:
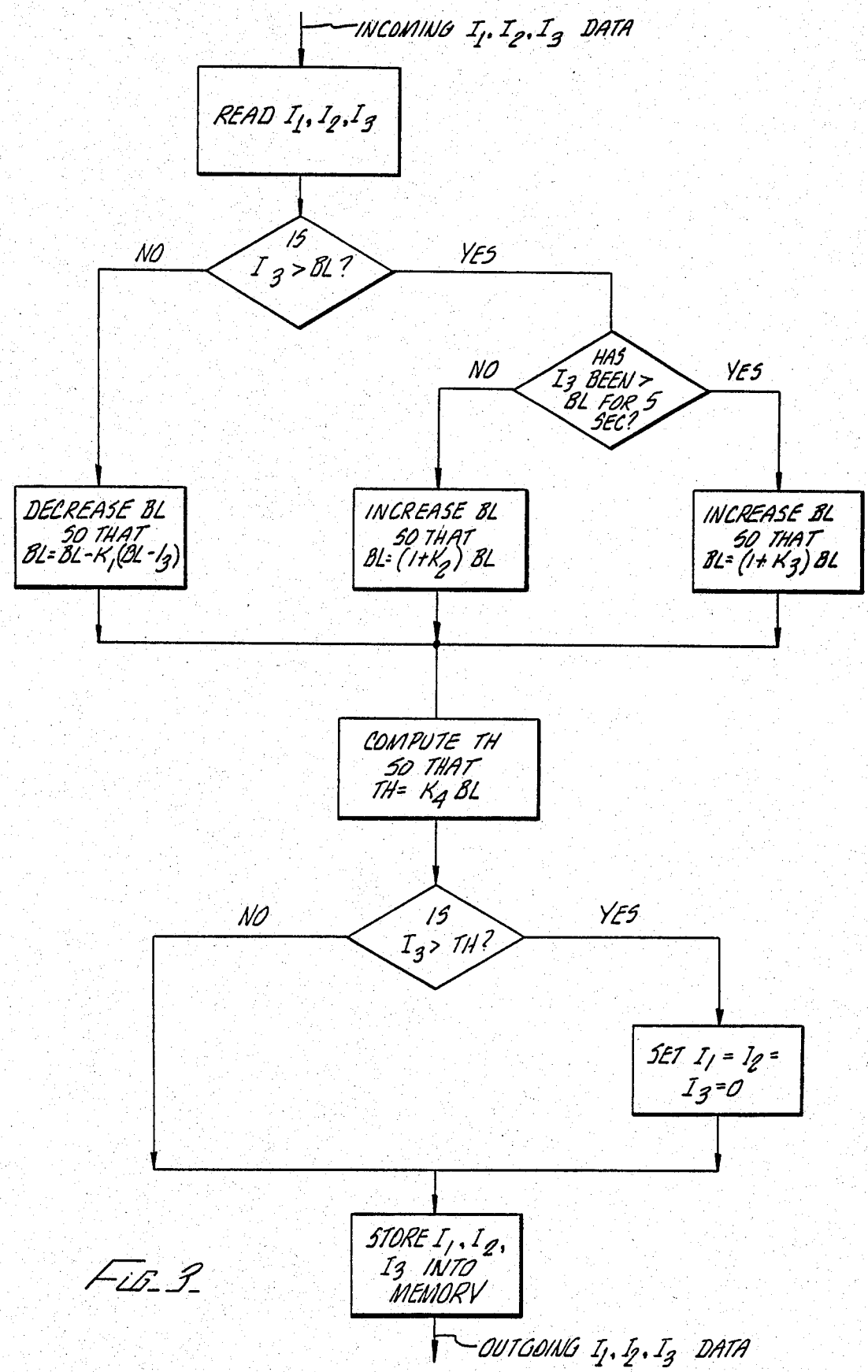
FIG. 3 is an exemplary flow diagram for implementing the oxygen saturation measuring apparatus in accordance with the present invention.

Turning now to FIG. 3, a signal filter method flow diagram as shown therein implemented within the apparatus 10 of FIG. 1 advantageously removes from the signals the portions thereof which are indicative of erroneous or unsuitable radiation readings. More particularly, and with continued reference to FIGS. 1 and 3, the central processor 14 reads from the system bus 12 the radiation itensities from the catheter tip at, for example, approximately four millisecond intervals and the control processor 14 sums each of the radiation intensities individually for a period of time which can be approximately 32 milliseconds. This initially averages the individual radiation intensities and thus slightly smoothes radiation intensities $I_1$, $I_2$ and $I_3$. The central processor 14 then compares the intensity $I_3$ with a base line intensity value which may be temporarily stored within the memory 58.

If the intensity $I_3$ is not greater than the base line intensity value, the central processor 14 decreases the base line value according to the following equation:

$$BL = BL - K_1 \cdot (BL - I_3)$$

where BL is the base line intensity value and $K_1$ is a predetermined constant which can equal approximately 0.25 in an exemplary embodiment.

Once the new base line intensity value is determined, a threshold intensity value is determined wherein $TH = K_4 \cdot BL$, where TH is the threshold intensity value and $K_4$ is a predetermined constant which can equal, for example, approximately 1.5. Once the threshold intensity value TH is calculated, the $\lambda_3$ intensity $I_3$ is compared with the threshold intensity value. If the intensity $I_3$ is not greater than the threshold intensity value, then the intensities $I_1$, $I_2$, and $I_3$ are stored by the central processor 14 into the memory 58. In the embodiment of FIG. 1, each intensity $I_1$, $I_2$, and $I_3$ are stored into the memory 58 and may further be separately accumulated to each form of weighted moving average for the respective wavelengths with a period of approximately five seconds.

However, if the intensity $I_3$ is greater than the threshold intensity value, then the central processor 14 sets each intensity $I_1$, $I_2$ and $I_3$ to zero and stores these zero values into memory as part of the aforementioned weighted moving averages. It is to be noted that because equation 8 referred to above from the referenced Shaw, et al., patent is based on ratios of reflected radiation intensities, the accumulation of zero individual radiation intensity values $I_1$, $I_2$, and $I_3$ has no influence on the ultimately calculated blood oxygen saturation.

With continued reference to FIGS. 1 and 3, if the central processor 14 determines that the intensity $I_3$ is greater than the base line intensity value, the central processor 14 then determines whether the intensity $I_3$ has been greater than the base line intensity value for a predetermined time period which can be approximately five seconds, although other time lengths may be suitably selected. This may be accomplished, for example, by programming the central processor 4 to measure a time interval in a fashion which is well known to those skilled in the art. If the intensity $I_3$ has not been greater than the base line intensity value for the five second time period, then the central processor 14 determines a new base line intensity value according to $BL=(1+K_2) \cdot BL$, where $K_2$ is a predetermined constant that can be, for example, approximately 0.004. The new base line intensity value is then used to calculate a new threshold intensity value which is compared to the intensity $I_3$ as described above.

If, however, the intensity $I_3$ has been greater than the base line intensity value for the predetermined time period, then the base line intensity value is increased so that $BL=(1+K_3) \cdot BL$, where $K_3$ is a predetermined constant that can have an exemplary value of approximately 0.120. Once the base line intensity value has been adjusted in this way, then the threshold intensity value is again determined and the remaining steps are performed by the central processor 14 as described above.

Thus, it is apparent that the method of FIG. 3 as implemented by the apparatus 10 of FIG. 1 adjusts a base line intensity value which generally follows the low-level portions of the $\lambda_3$ intensity $I_3$. As seen in FIG. 2, the $\lambda_3$ intensity $I_3$ plotted as the curve 58 thus may be thought to generally ride along or in relatively close proximity to a base line intensity value represented by a curve 62. The base line intensity value is continually updated in order to maintain this relationship. If the $\lambda_3$ intensity 58 is not greater than the base line intensity value 62, the base line is gradually decreased. On the other hand, if the $\lambda_3$ intensity 58 is greater than the base line intensity value 62, then the base line intensity value is increased by an amount related to the length of time that the $\lambda_3$ intensity has exceeded the base line intensity value. More particularly, if the $\lambda_3$ intensity 58 has been greater than the base line intensity value for not longer than the predetermined time period, then the base line intensity value is slightly increased for each $\lambda_3$ intensity comparison. However, if the $\lambda_3$ intensity $I_3$ has been greater than the base line intensity value for longer than the predetermined time period, then the base line intensity value is increased relatively quickly with respect to the previous base line intensity value to thereby quickly adjust the base line intensity value with respect to the $\lambda_3$ intensity.

Once the base line intensity value is adjusted in this way, then the threshold intensity value represented by the dashed line 64 in FIG. 2 is determined with respect to the base line intensity value. If the $\lambda_3$ intensity 58 is greater than the threshold intensity value 64, the $\lambda_1$, $\lambda_2$ and $\lambda_3$ intensities $I_1$, $I_2$ and $I_3$ are set to zero and are then stored into the memory 58 as part of a moving average accumulation. Conversely, if the $\lambda_3$ intensity is not greater than the threshold intensity value, then the $\lambda_1$, $\lambda_2$ and $\lambda_3$ intensities read by the central processor 14 from the optical module interface 16 are then stored into the memory 58 as part of the moving average accumulation. In this way, the threshold intensity value determines the level above which the $\lambda_3$ intensity $I_3$ in particular and the associated $\lambda_1$ and $\lambda_2$ intensities $I_1$ and $I_2$ are presumed to be invalid. The moving average values for the intensities $I_1$, $I_2$ and $I_3$ are then used to determine oxygen saturation as described above.

It is to be understood that the predetermined constants $K_1$-$K_4$ can be varied according to the particular system requirements. Moreover, the adjustments to the base line intensity value can be fixed rather than related to the constants $K_1$-$K_3$ which will be readily apparent to those skilled in the art. It will be further apparent that the base line intensity value BL can be written in terms of the threshhold intensity value TH and the threshold intensity value TH can therefore be considered to be adjusted directly with respect to the intensity $I_3$.

Thus, the signal filter method of FIG. 3 and the apparatus 10 of FIG. 1 provide an improved oximeter apparatus less susceptible to the pulsatile reflected radiation intensities indicative or erroneous or unuseable data. The steps set forth in FIG. 3 can, of course, be implemented using well-known software techniques with the central processor 14.

Figure 4:
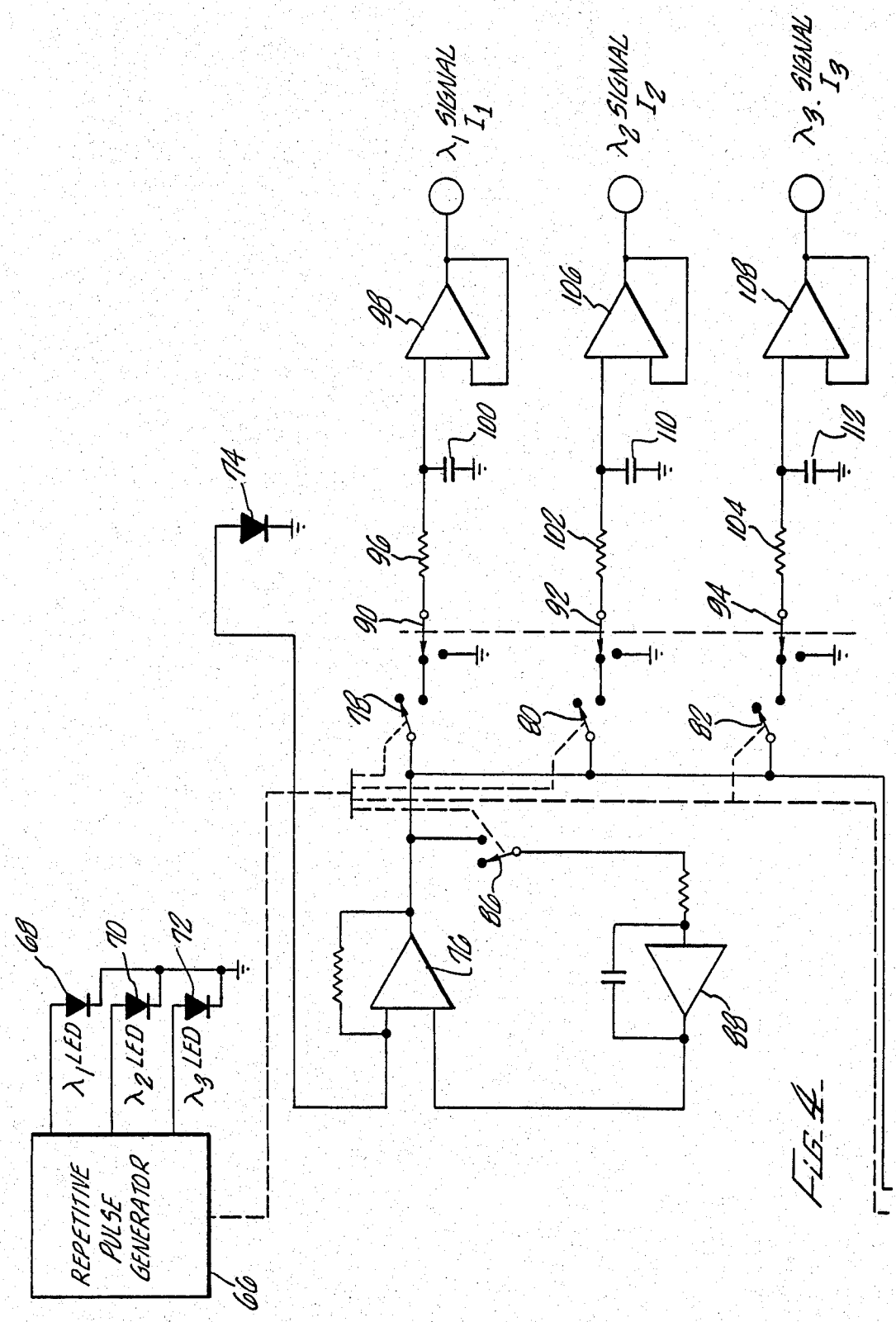
FIG. 4 is a portion of FIG. 1 of the Shaw, et al., patent referenced above modified for use with an alternative embodiment of the present invention.
Figure 5:
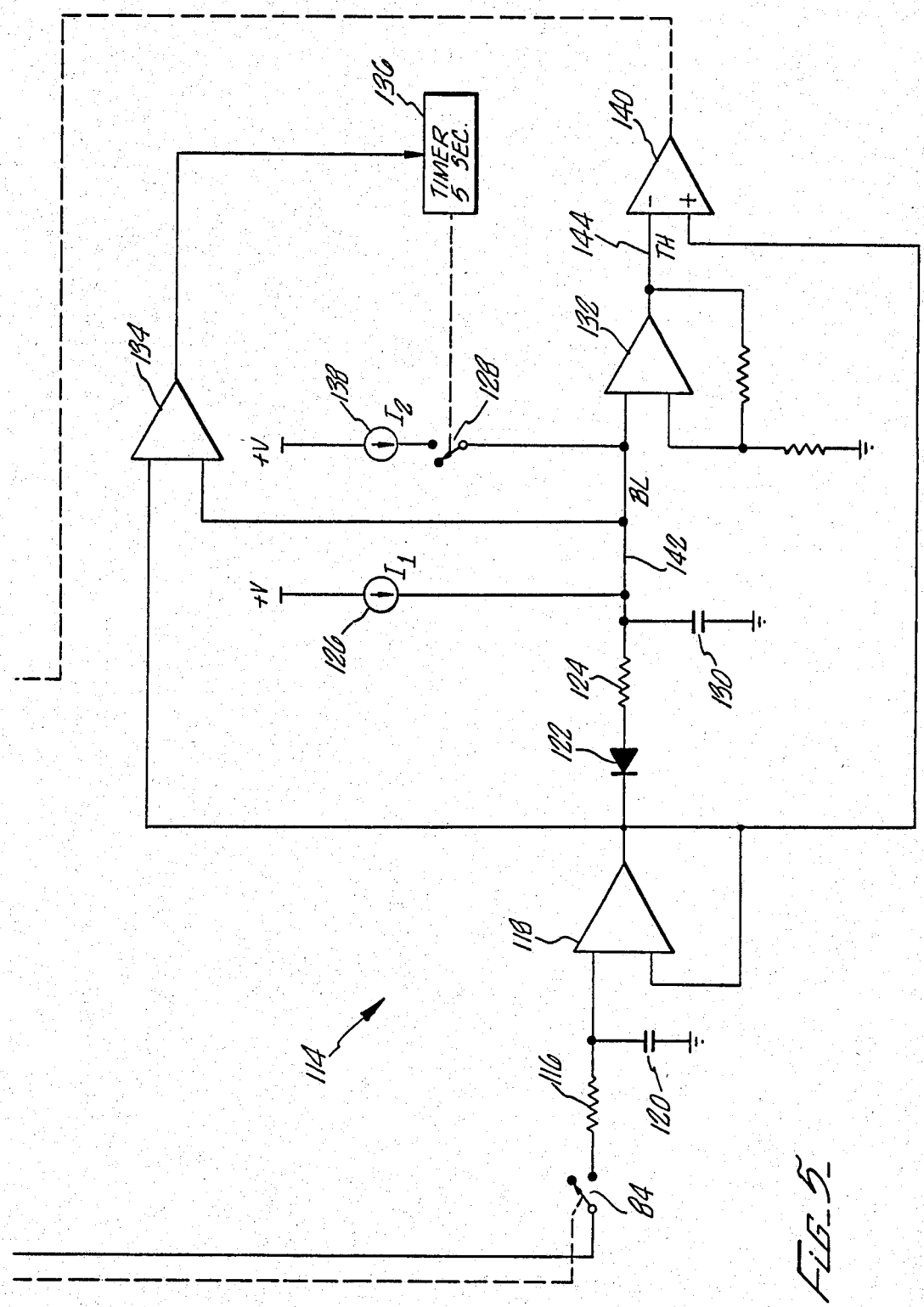
FIG. 5 is an alternative embodiment of a signal filter useful with the present invention and adapted for use with the modified circuitry of FIG. 4.

With reference now to FIGS. 4 and 5, the apparatus disclosed in the referenced Shaw, et al., patent may be modified to incorporate the signal filter in accordance with the present invention.

As shown in FIG. 4, such an apparatus includes a repetitive pulse generator 66 which sequentially energizes a plurality of light-emitting diodes (LED's) 68, 70 and 72. The LEDs 68, 70 and 72 are coupled through a suitable optical combiner, optical integrator, and catheter as, for example, shown in FIG. 1, to provide to a detector 74 back-scattered and reflected radiation from the catheter tip. The LEDs 68, 70 and 72 emit radiation at three predetermined wavelengths $\lambda_1$, $\lambda_2$ and $\lambda_3$ as previously described above with reference to FIG. 1.

The detector 74 provides a signal representative of the radiation from the catheter tip to an amplifier 76, the output of which is connected to a plurality of normally open switches 78, 80, 82, 84 and 86 (FIGS. 4 and 5). The switches 78 and 80 are controlled by the generator 66 so as to be closed during the time that the LED's 68 and 70, respectively, emit radiation. Similarly, the switches 82 and 84 are controlled by the generator 66 so as to be closed during the portion of time that the LED 72 emits radiation. Lastly, the switch 86, as controlled by the generator 66, is closed when none of the LED's 68–72 is emitting, thus forming a closed loop servo system between the amplifier 76 and an amplifier 88 which establishes a bias voltage on the amplifier 76 that adjusts its output voltage to zero.

The switches 78–82 are in turn connected to normally closed switches 90–94 respectively. The switch 90 is connected through a resistor 96 to an amplifier 98 and a capacitor 100. Similarly, the switches 92 and 94 are connected through resistors 102 and 104 to amplifiers 106 and 108 and to capacitors 110 and 112. The amplifiers 98, 106 and 108 provide $\lambda_1$, $\lambda_2$ and $\lambda_3$ radiation intensity output signals $I_1$, $I_2$ and $I_3$, respectively.

As shown with reference to FIG. 5, the switch 84 connects the signal from the amplifier 76 to signal filter circuitry designated generally 114. The switch 84 is connected through a resistor 116 to an amplifier 118 and a capacitor 120. The output of the amplifier 118 is connected to the anode of a diode 122, the cathode of which is connected through a resistor 124 via a line 142 to a first current source 126, a switch 128, a capacitor 130, an amplifier 132 and a comparator 134. The output of the amplifier 118 is also connected to a second input of the comparator 134. The output of the comparator 134 controls a timer 136 which in turn controls the switch 128. The switch 128 is also connected to a second current source 138. The output of the amplifier 132 is connected through a line 144 to the inverting input of a comparator 140, the non-inverting input of which is connected to the output of the amplifier 118. The output of the comparator controls the position of the switches 90, 92 and 94.

In operation, when the LED 72 emits radiation and the switches 82 and 84 are closed, the radiation from the catheter is detected by the detector 74. The detector 74 output is amplified by the amplifier 76 which applies a signal through the switch 84 to the amplifier 118. The current source 126 continuously provides current to the line 142 the signal on this line being proportional to a base line intensity value (BL), hereinafter referred to as a base line signal. The current source 126 increases the base line signal by a predetermined amount with respect to time, that is to say, at a predetermined rate. This base line signal is scaled or multiplied by the amplifier 132 to provide a threshold signal (TH) on the line 144 to the comparator 140.

When the output of the amplifier 118 is less than the base line signal on the line 142, the capacitor 130 discharges through the resistor 124 and the diode 122 to thus decrease the base line signal on the line 142 and in turn proportionally decrease the threshold signal on the line 144. If the output of the amplifier 118 is greater than the base line signal, however, then the current source 126 provides a first current to the line 142 to thereby increase the base line signal. Furthermore, if the output of the amplifier 118 is greater than the threshold signal on the line 144, then the comparator 140 controls the switches 90–94 (FIG. 4) to connect the resistors 96, 102 and 104 to ground to thereby disable the further application of the signal from the amplifier 76 through the switches 78, 80 and 82. In this way, if the radiation intensity $I_3$ is greater than the threshold signal on the line 144, indicating the erroneous radiation information is returning from the catheter, the signals proportional to the radiation intensities $I_1$, $I_2$, and $I_3$ are removed from the inputs to the amplifiers 98, 106 and 108.

If the output of the amplifier 118 remains greater than the base line signal for more than five seconds, the comparator 134 and the timer 136 control the switch 128 to connect the second current source 138 to the line 142. The second current source 138 provides a fixed current to the line 142 which relatively quickly increases the base line signal thereon. As with the current source 126, the current source 138 increases the base line signal by a predetermined amount with respect to time, which is to say, at a predetermined rate.

Thus it is seen that the signal filter circuitry 114 provides a base line signal which generally follows the low-level portions of the radiation intensity $I_3$. A threshold signal is provided which is related to the base line signal, and if the radiation intensity $I_3$ is greater than this threshold signal, then the signals corresponding to the radiation intensities $I_1$, $I_2$ and $I_3$ are not applied to the respective amplifiers 98, 106, and 108. It is to be further noted that the circuitry 114 provides an analog implementation of the signal filter method of FIG. 3.

Having thus described one embodiment of our invention in detail, it is to be understood that numerous equivalents and alterations which do not depart from the invention will be apparent to those skilled in the art, given the teachings herein. Thus, our invention is not to be limited to the above description but is to be of the full scope of the appended claims.

What is claimed is:

1. An apparatus for determining oxygen saturation levels in blood comprising means for generating electromagnetic radiation at a plurality of different wavelengths, means coupled to said generating means for transmitting said electromagnetic radiation at each of said plurality of different wavelengths to the blood and for receiving electromagnetic radiation reflected back from the blood at each of said plurality of different wavelengths in response to said electromagnetic radiation so transmitted, a detector coupled to said receiving means for generating a plurality of signals respectively having values which vary in proportion to the intensities of said electromagnetic radiation received at each of said plurality of different wavelengths, means for monitoring said signals from said detector ro determine short time intervals when said signals increase substantially in value to indicate that said receiving means is receiving reflections from other than solely said blood, means for negating the effect of the signals received during said short time intervals, and means connected to receive said signals for generating an oxygen saturation output signal as a function of said signals except for the negated signals.

2. An apparatus according to claim 1 wherein said monitoring means includes means for establishing a base level for said signals, means for determining when at least one of said signals exceeds said base level by a predetermined amount or more.

3. An apparatus for determining oxygen saturation levels in blood comprising means for generating electromagnetic radiation at a plurality of different wavelengths, means coupled to said generating means for transmitting said electromagnetic radiation at each of said plurality of different wavelengths to the blood and for receiving electromagnetic radiation reflected back from the blood at each of said plurality of different wavelengths in response to said electromagnetic radiation so transmitted, a detector coupled to said receiving means for generating a plurality of analog signals respectively having values which vary in proportion to the intensities of said electromagnetic radiation received at each of said plurality of different wavelengths, means coupled to said detector for providing data signals corresponding to said analog signals at predetermined data time intervals, means for determining when said data signals substantially increase in value during short intervals in time, and means connected to receive said data signals and connected to receive an input from said determining means for generating oxygen saturation output signals as a function of said data signals minus the data signals generated during said short time intervals.

4. An apparatus according to claim 3 wherein said determining means includes means for establishing a base level for said signals, means for determining when at least one of said signals exceeds said base level by a predetermined amount, and means for determining said short intervals in time by the number of consecutive signals received which all exceed said base level by said predetermined amount or more.

5. An apparatus for determining oxygen saturation levels in blood comprising means for generating electromagnetic radiation at a plurality of different wavelengths, means coupled to said generating means for transmitting said electromagnetic radiation at each of said plurality of different wavelengths to the blood and for receiving electromagnetic radiation reflected back from the blood at each of said plurality of different wavelengths in response to said electromagnetic radiation so transmitted, a detector coupled to said receiving means for generating a plurality of signals respectively having values which vary in proportion to the intensities of said electromagnetic radiation received at each of said plurality of different wavelengths, means coupled to said detector for generating an oxygen saturation output signal is a function of said signals, and means for determining and filtering out of the signals transmitted to the output signal generating means those signals received during the short intervals in time when the intensity of the signals substantially increases in value above the average level of the signals.

6. An apparatus according to claim 5 wherein said determining and filtering means includes means for establishing a base level for said signals, means for determining when at least one of said signals exceeds said base level by a predetermined amount, and means for determining said short intervals in time by the number of consecutive signals received which all exceed said base level by said predetermined amount or more.

7. An apparatus for determining oxygen saturation level in blood comprising means for generating electromagnetic radiation at a plurality of different wavelengths, means coupled to said generating means for transmitting said electromagnetic radiation at each of said plurality of different wavelengths to the blood and for receiving electromagnetic radiation reflected back from the blood at each of said plurality of different wavelengths in response to said electromagnetic radiation so transmitted, a detector coupled to said receiving means for generating a plurality of signals respectively having values which vary in proportion to the intensities of said electromagnetic radiation received at each of said plurality of different wavelengths, means for monitoring one of said signals from said detector to determine short time intervals when said one signal increases substantially in value to indicate that said receiving means is receiving reflections from other than solely said blood, means for negating the effect of the signals received during said short intervals, and means connected to receive said signals for generating an oxygen saturation output signal as a function of said signals except for the negated signal.

8. An apparatus according to claim 7 wherein said monitoring means includes means for establishing a base level for said one signal, means for determining when said one signal exceeds said base level by a predetermined amount, and means for determining said short intervals in time by the number of consecutive signals received which all exceed said base signal by said predetermined amount or more.

* * * * *